(12) United States Patent
Kaiser, II

(10) Patent No.: US 10,005,698 B2
(45) Date of Patent: Jun. 26, 2018

(54) FERTILIZER COMPOSITION AND METHOD FOR SUSPENDING FERTILIZER IN AN AQUEOUS SOLUTION

(71) Applicant: BFP Management, LLC, Salt Lake City, UT (US)

(72) Inventor: James Parker Kaiser, II, Pleasant Grove, UT (US)

(73) Assignee: BFP Management, LLC, Salt Lake City, UT (US)

( * ) Notice: Subject to any disclaimer, the term of this patent is extended or adjusted under 35 U.S.C. 154(b) by 110 days.

(21) Appl. No.: 15/147,117

(22) Filed: May 5, 2016

(65) Prior Publication Data

US 2016/0244381 A1  Aug. 25, 2016

Related U.S. Application Data

(62) Division of application No. 13/764,654, filed on Feb. 11, 2013, now Pat. No. 9,334,200.

(Continued)

(51) Int. Cl.
  *C05G 3/00* (2006.01)
  *B01L 99/00* (2010.01)
  (Continued)

(52) U.S. Cl.
  CPC ............ *C05G 3/007* (2013.01); *A01C 23/008* (2013.01); *A01C 23/042* (2013.01); *A01C 23/047* (2013.01); *B01L 99/00* (2013.01); *B82Y 35/00* (2013.01); *C05B 1/02* (2013.01); *C05B 9/00* (2013.01); *C05C 1/00* (2013.01);
  (Continued)

(58) Field of Classification Search
  CPC .. G01N 5/10; G01N 2015/0038; B82Y 35/00; B82Y 30/00; C05G 1/00; C05G 3/0005; C05G 3/007; C05C 5/02; C05C 9/00; C05C 5/04; C05C 1/00; C05B 9/00; C05B 1/02; A01C 23/008; A01C 23/042; A01C 23/047; B01L 99/00; Y10S 977/775; Y10S 977/88; Y10S 977/902; Y10S 977/773; H01J 49/0027; Y02P 60/214
  See application file for complete search history.

(56) References Cited

U.S. PATENT DOCUMENTS 7,563,457 B2   7/2009  Cha et al.
8,568,758 B2  10/2013  Daniels
(Continued)

FOREIGN PATENT DOCUMENTS

CN      1451636 A    10/2003
WO  2006086654 A2     8/2006
WO  2013118131 A1     8/2013

OTHER PUBLICATIONS

E. Corradini et al.: "A preliminary study of the incorporation of NPK fertilizer into chitosan nanoparticles," Express Polymer Letters, vol. 4, No. 8, Jan. 1, 2010, pp. 509-515.
(Continued)

*Primary Examiner* — Jennifer A Smith
(74) *Attorney, Agent, or Firm* — Terrence J. Edwards; TechLaw Ventures, PLLC

(57) ABSTRACT

A system and method for providing fertilizer for crop production in an aqueous solution comprising nano-sized fertilizer particles, which are free of any chemical side chain and free any micelle to protect the nano-sized particle from re-agglomeration, suspended therein for improved uptake by the population of the crop.

9 Claims, 4 Drawing Sheets

Related U.S. Application Data

(60) Provisional application No. 61/757,675, filed on Jan. 28, 2013.

(51) Int. Cl.

| | | |
|---|---|---|
| *A01C 23/00* | (2006.01) | |
| *A01C 23/04* | (2006.01) | |
| *C05B 1/02* | (2006.01) | |
| *C05B 9/00* | (2006.01) | |
| *C05C 1/00* | (2006.01) | |
| *C05C 5/02* | (2006.01) | |
| *C05C 5/04* | (2006.01) | |
| *C05C 9/00* | (2006.01) | |
| *C05G 1/00* | (2006.01) | |
| *B82Y 35/00* | (2011.01) | |
| *G01N 15/10* | (2006.01) | |
| *B82Y 30/00* | (2011.01) | |
| *G01N 15/00* | (2006.01) | |
| *H01J 49/00* | (2006.01) | |

(52) U.S. Cl.
CPC ............... *C05C 5/02* (2013.01); *C05C 5/04* (2013.01); *C05C 9/00* (2013.01); *C05G 1/00* (2013.01); *C05G 3/0005* (2013.01); *G01N 15/10* (2013.01); *B82Y 30/00* (2013.01); *G01N 2015/0038* (2013.01); *H01J 49/0027* (2013.01); *Y02P 60/214* (2015.11); *Y10S 977/773* (2013.01); *Y10S 977/775* (2013.01); *Y10S 977/88* (2013.01); *Y10S 977/902* (2013.01)

(56) References Cited

U.S. PATENT DOCUMENTS

| | | |
|---|---|---|
| 9,334,200 B2 | 5/2016 | Kaiser, II |
| 2002/0068092 A1 | 6/2002 | Bosch et al. |
| 2003/0087308 A1 | 5/2003 | Lindner et al. |
| 2010/0072295 A1 | 3/2010 | Usmar et al. |
| 2010/0273896 A1 | 10/2010 | Lo et al. |
| 2011/0160920 A1 | 6/2011 | Orr et al. |
| 2011/0296885 A1 | 12/2011 | Nilwala et al. |
| 2013/0078469 A1 | 3/2013 | Winter et al. |
| 2014/0208815 A1 | 7/2014 | Kaiser, II |

OTHER PUBLICATIONS

Hiroaki Mochizuki et al.: "Increasing fertilizer and pesticide use efficiency by nanotechnology in desert afforestation, arid agriculture," Jun. 1, 2009; Retrieved from the Internet: http://nodaiweb.university.jp/desert/pdf9/Poster Session 2 Stress Biology and Desert Agriculture/Hiroaki Mochizuki pp129-132.pdf [retrieved on Feb. 9, 2017].

Prapatsorn Boonyanitipong et al.: "Toxicity of ZnO and TiO2 Nanoparticles on Germinating Rice Seed Oryza Sativa L," International Journal of Bioscience, Biochemistry and Bioinformatics, Nov. 30, 2011; Retrieved from the internet: http://www.ijbbb.org/papers/53-B107.pdf [retrieved on Feb. 10, 2017].

Chih-Ping Tso et al.: "Sability of metal oxide nanoparticles in aqueous solutions," Water Science and Technology, vol. 61, No. 1, Jan. 1, 2010, p. 127.

Lu Yu, et al. "Update of Perchlorate in Terrestrial Plants," Ecotoxicology and Environmental Safety, vol. 58, Issue, 1, May 2004, pp. 44-49.

FERTILIZER COMPOSITION AND METHOD FOR SUSPENDING FERTILIZER IN AN AQUEOUS SOLUTION

CROSS-REFERENCE TO RELATED APPLICATIONS

This application is a divisional of U.S. application Ser. No. 13/764,654, filed Feb. 11, 2013 (now U.S. Pat. No. 9,334,200, issued May 10, 2016) and claims the benefit of U.S. Provisional Application No. 61/757,675, filed Jan. 28, 2013, which are hereby incorporated by reference herein in its entirety, including but not limited to those portions that specifically appear hereinafter, the incorporation by reference being made with the following exception: In the event that any portion of the above-referenced applications are inconsistent with this application, this application supersedes said above-referenced applications.

STATEMENT REGARDING FEDERALLY SPONSORED RESEARCH OR DEVELOPMENT

Not Applicable.

BACKGROUND

The disclosure relates generally to fertilizer compositions, and more particularly, but not necessarily entirely, to distributing the fertilizer compositions comprising various amounts or concentrations of nitrogen, phosphorous and potassium, as well as any other ingredients which may be present in fertilizer compositions such as calcium, magnesium, sulfur, boron, chlorine, iron, manganese, molybdenum, zinc, nickel, and other various nutrients, which may by distributed within an aqueous solution. Current fertilization systems generally provide fertilizer in forms that are not readily usable to plant cells. Accordingly, it is common in the farming industry to provide much more of the fertilizer composition than is actually used by the plant. Such practices have negative impacts on the environment, require excess transport of chemicals that will not be used, and ultimately increases the cost of farming.

The features and advantages of the disclosure will be set forth in the description which follows, and in part will be apparent from the description, or may be learned by the practice of the disclosure without undue experimentation. The features and advantages of the disclosure may be realized and obtained by use of the instruments and combinations particularly pointed out in the appended claims.

BRIEF DESCRIPTION OF THE DRAWINGS

The features and advantages of the disclosure will become apparent from a consideration of the subsequent detailed description presented in connection with the accompanying drawings in which.

DETAILED DESCRIPTION

Figure 1:
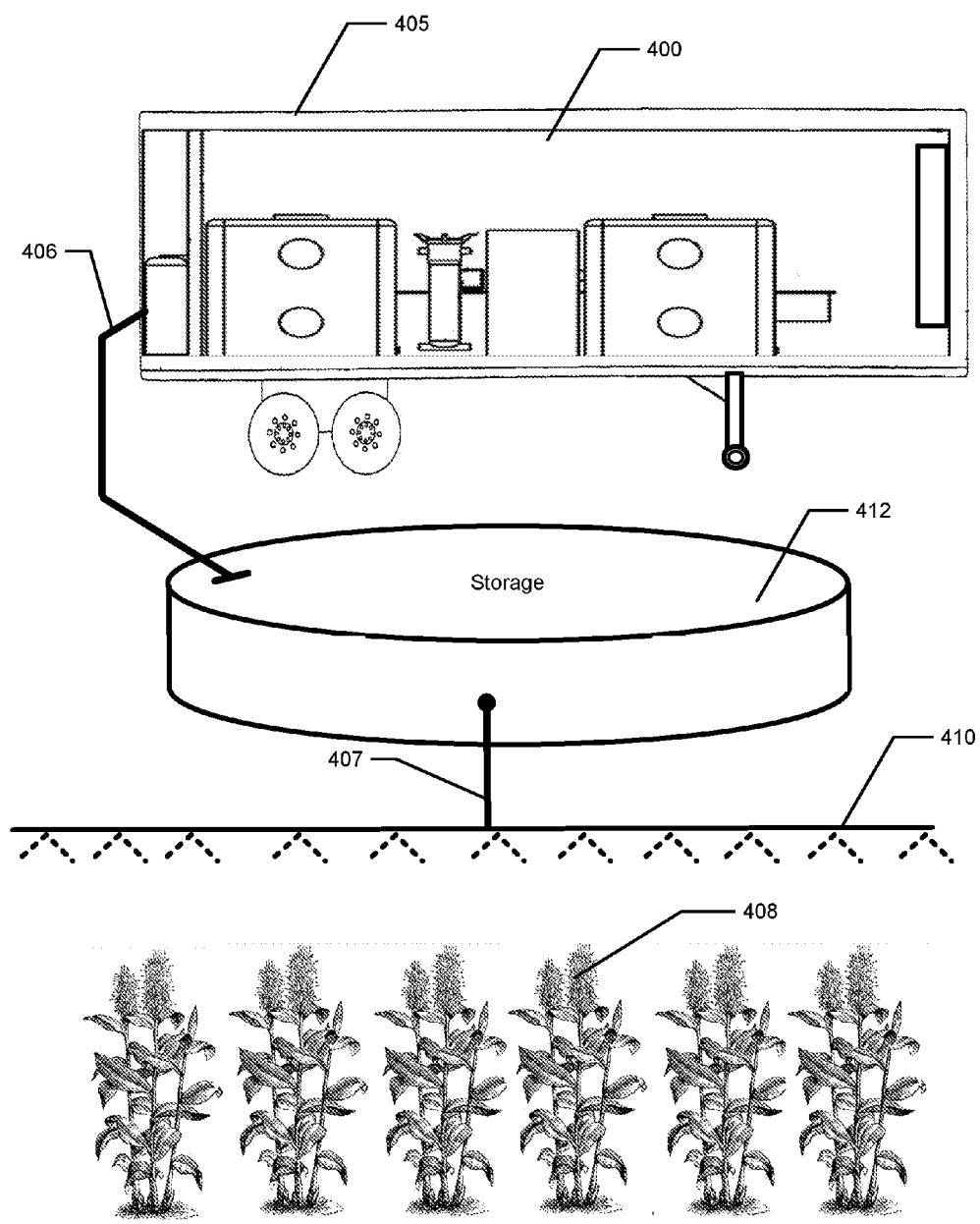
FIG. 1 is a schematic view of a mobile fertilizer particulation system made in accordance with the principles of the disclosure.

For the purposes of promoting an understanding of the principles in accordance with the disclosure, reference will now be made to the implementations and embodiments illustrated in the drawings and specific language will be used to describe the same. It will nevertheless be understood that no limitation of the scope of the disclosure is thereby intended. Any alterations and further modifications of the inventive features illustrated herein, and any additional applications of the principles of the disclosure as illustrated herein, which would normally occur to one skilled in the relevant art and having possession of this disclosure, are to be considered within the scope of the disclosure claimed.

Before the fertilizer compositions and methods for suspending the fertilizer compositions in an aqueous solution are disclosed and described, it is to be understood that this disclosure is not limited to the particular configurations, process steps, ingredients and materials disclosed herein as such configurations, process steps, ingredients, and materials may vary somewhat. It is also to be understood that the terminology employed herein is used for the purpose of describing particular embodiments and implementations only and is not intended to be limiting since the scope of the disclosure will be limited only by the appended claims and equivalents thereof.

The publications and other reference materials referred to herein to describe the background of the disclosure, and to provide additional detail regarding its practice, are hereby incorporated by reference herein in their entireties, with the following exception: In the event that any portion of said reference materials is inconsistent with this application, this application supersedes said reference materials. The reference materials discussed herein are provided solely for their disclosure prior to the filing date of this application. Nothing herein is to be construed as a suggestion or admission that the inventors are not entitled to antedate such disclosure by virtue of prior disclosure, or to distinguish the disclosure from the subject matter disclosed in the reference materials.

In describing and claiming the subject matter of the disclosure, the following terminology will be used in accordance with the definitions set out below.

It must be noted that, as used in this specification and the appended claims, the singular forms "a," "an," and "the" include plural referents unless the context clearly dictates otherwise.

As used herein, the terms "comprising," "including," "containing," "characterized by," and grammatical equivalents thereof are inclusive or open-ended terms that do not exclude additional, unrecited elements or method steps.

As used herein, the phrase "consisting of" and grammatical equivalents thereof exclude any element, step, or ingredient not specified in the claim.

As used herein, the phrase "consisting essentially of" and grammatical equivalents thereof limit the scope of a claim to the specified materials or steps and those that do not materially affect the basic and novel characteristic or characteristics of the claimed disclosure.

As used herein, the term "ultrapure water" is intended to mean water that has been purified such that it measures at least 0.5 mega ohms of resistance, and may include water having a designation to those skilled in the art of "ultrapure water." Pure water is intended to denote water that is relatively reactive (when compared to water having contaminants therein) with its surroundings due primarily to the polarized nature of water molecules. For example: it should be noted that, water, a tiny combination of three nuclei and ten electrons possesses special properties that make it unique among the more than 15 million chemical species we are presently aware of and essential to all life. A water molecule is electrically neutral, but the arrangement of the hydrogen atoms and the oxygen atom is such that a charge displacement is created thus constituting an electric dipole, or polar molecule, with one end (the end with the hydrogen atom) being positive and the other end (the end with the oxygen atom) being negative. Because, opposite charges attract, the negative end of one water molecule will tend to orient itself in a fashion that will bring it close to the positive end of another molecule that is nearby. Generally speaking, this dipole-dipole attraction is less than that of a normal chemical bond, and is dynamic in nature. Further, this attraction causes complex structures that are temporary in nature and thus always changing. The various structures can be influenced by other elements (contaminants) that can provide electrical balance for these structures, thereby stabilizing the structures and making a body of water less reactive.

Water is a unique compound that has many different chemical and physical properties. For example, water molecules may include any or all of the following bonding types. In water, a strong hydrogen bond is present with the OH covalent bond within the water molecule. A weak hydrogen bond is the bond between two water molecules. This weak hydrogen bond is also responsible for water bonding with ammonia, for example (thus ammonia's remarkably high solubility in water). Water also includes ionic attraction due to their positive and negative ions. By way of example, sodium ions and chlorine ions have an ionic attraction, which will form an ionic bond creating sodium chloride. Water also experiences permanent dipole moments, H2O, NH3, and PC13 are examples of molecules with a permanent dipole moment. Water may also include ion-dipole interactions. Sodium ions in water will create an ion-dipole interaction where the dipole will orient its' negative side towards the sodium (a positive ion). Chlorine ions conversely will create an ion-dipole interaction where the dipole will orient its' positive side towards the chlorine (a negative ion). Water may also experience dipole-dipole interactions. Dipoles will orient themselves with their negatively charged side towards the other's positively charged side. Water may also experience ion-induced dipole interactions. Nearby ions can distort electron clouds (even in dipoles) temporarily changing their dipole moments. This effect is particularly strong in larger ions such as SO22—this action can play a dominant role in compound formation. Water may also experience dipole-induced dipole interactions. Hydrocarbons, which are non-polar in nature, may create an example of a dipole (in this case water) creating a hydrate compound as the water dipole creates a temporary dipole out of the non-polar species (the hydrocarbons). Water may also experience dispersion (London force) interactions. These dipole independent forces are evidenced when we consider that nitrogen as N2 may be condensed to liquids or solids.

It will be understood that ultrapure water contains virtually no inorganic matter, such as cations, anions, solids, nor does it contain organic matter, such as carbon based material. The ASTM definition for ultrapure water, as it relates to resistivity, is shown below and this disclosure includes through type E-4:

| Parameter | Type E-1 | Type E-1.1 | Type E-1.2$^B$ | Type E-1.3$^B$ | Type E-2 | Type E-3 | Type E-4 |
|---|---|---|---|---|---|---|---|
| Resistivity, 25° C. | 18.3 | 18.2 | 18.2 | 18.2 | 16.5 | 12 | 0.5 |

Ultrapure water may be established using any known protocol, but one exemplary multi-stage process begins with: carbon filtration, softening, reverse osmosis, deionization, exposure to ultraviolet light or radiation, and submicron filtration. A standard step is that once the ultrapure water has been established, then the ultrapure water is resent through the deionization process to maintain its resistivity and reactivity.

As used herein, "effective amount" means an amount of a component of the fertilizer compound that is nontoxic but sufficient to provide the desired effect and performance at a reasonable benefit/risk ratio attending any fertilizing compound and/or composition. For example, an effective amount of a fertilizer compound is an amount sufficient to promote the optimal or desired maturation of crops.

As used herein, "manipulated" refers to using existing fertilizer that is on the premises of the agricultural entity, such as farmers, and has thus already been purchased. The term "manipulated" also includes changing the fertilizer's chemical state or size, such as decreasing the average compound size from a macro or micro size to a nano size, which is 100 nanometers or less, through mixing or in some fashion altering the concentrations of the fertilizer. As used herein, "manipulating" does not include manufacturing fertilizer or anything that falls within the agricultural industry's understanding of services that fall within the scope of manufacturing, such as bringing fertilizer onto the agricultural entity's premises, such as farms, because that is understood to be a manufacturing function.

In an implementation the effective concentration of a nanoparticulated fertilizer may be 0.053% of the amount of standard fertilizer for the same field size wherein the established standard fertilizer usage is 40 gallons per treatment for 33 acres. Typically a treatment is 40 gallons of standard fertilizer, which equals 151.416 liters of standard fertilizer. In the implementation, 10 gallons of ultrapure water with nanoparticulated fertilizer mixed therein is estimated and shown to achieve better results than the massive amount of standard fertilizer. It will be appreciated that there is no general typical application or amount because those in the agricultural industry, such as farmers, will use varying amounts in relation to quantities of fertilizer that may be used in an application. Thus, the disclosure contemplates a typical reduction in the gallons of fertilizer used in the treatment of crops by amounts approaching a 50% reduction of any individual farmer's protocol. Further, the disclosure contemplates formulating, manipulating, and/or using a standard fertilizer and reducing the amount used to less than 5% of the actual standard fertilizer contained in the ultrapure water, which makes up the quantity of an amount of liquid approaching the 50% reduction of the farmers protocol for fertilizing.

In an implementation an amount of particulated fertilizer used may be 0.08 liters of particulated standard fertilizer suspended in 20 gallons ultrapure water. Accordingly, 0.08/151.416 equals 0.053% of the normal standard fertilizer usage for the same application.

In an implementation a field or acreage that may typically require 40 gallons of untreated or standard fertilizer, may only be fertilized with nanoparticulated fertilizer comprising 0.157% of the amount of standard fertilizer in a 20 gallon solution for achieving the same results for the same field size. Accordingly, systems and methods disclosed herein may result in the use of use of fertilizer in a range of about 0.02% of the established use of standard fertilizer as a projected minimum, to a maximum projected use of about 5% of the established use of standard fertilizer in a 20 gallon solution.

By way of example, a standard 9-24-3 fertilizer was applied to a 33 acre seeded plot using 40 gallons per application. A separate 33 acre plot was seeded 7 days later and used the composition of the disclosure, which includes the manipulated (nanoparticulated) 9-24-3 fertilizer. Only 20 gallons of the manipulated fertilizer were used per application and the relative amount of manipulated fertilizer comprised about 0.157 liters of the manipulated fertilizer, which was concentrated into the 20 gallons of fluid. Both fields were analyzed on the same date to determine the rate of growth and the quality of the growth. After 46 days from planting (46 days post planting), the field that used the 40 gallons of standard fertilizer grew at an anticipated rate. On the other hand, the field that used the 20 gallons of manipulated or nanoparticulated fertilizer (which was 39 days post planting since it was seeded 7 days later) grew at a rate that exceeded the 40 gallon standard fertilizer.

In the above examples, 40 gallons of standard fertilizer (in the form of a traditional liquid fertilizer) and 10 gallons of manipulated fertilizer and 20 gallons of manipulated fertilizer. The manipulated fertilizer started with the traditional liquid fertilizer and then nanoparticulated the standard fertilizer and introduced it into the 10 and 20 gallons of ultrapure water, respectively. The size of the liquid (standard fertilizer) used in the above examples was shown to be over 5000 nanometers before the manipulation occurred, which reduced the average size of the compound to 100 nanometers or less. The results of the example show that there is more rapid growth and a higher quality growth in the plant using the 10 gallons or 20 gallons of manipulated fertilizer than there was in the 40 gallon standard fertilizer.

The success may be attributable to the fact that the manipulated, nanoparticulated fertilizer is comprised of compounds that are less than 100 nanometers in at least one dimension, whereas standard fertilizer comprises compounds that are very large in comparison and may substantially larger than 100 nanometers and may be over 5,000 nanometers in at least one dimension. It is understood that plant and animal cells uptake a chemical moiety and compounds that are less approximately 100 nanometers or less without further breakdown required. Thus, use of the nanoparticulated fertilizer of the disclosure may result in instant access to the plant cells of the desired fertilizer, thus increasing growth and maturation of the plant, while reducing runoff and leaching of undesirable chemicals into surrounding soil and water systems.

With reference primarily to FIG. 1, a mobile lab system for providing nanoparticulated fertilizer to crops within a farming environment will be discussed. As can be seen in the figure, a lab 400 may be disposed within a transportable and locate proximal to a crop 408 having a population of individual plants that may be treated simultaneously or individually according to the implementation and needs of the crop 408. In an implementation, the lab 400 may produce a fertilizer composition that is intended for distribution to the crop 408 through liquid dispersion system such as an irrigation system 410. In an implementation, the lab 400 may be fluidly connected or in fluid communication with a holding or storage tank, facility or other container 412 via fluid connector 406. The container 412 may be in fluid communication with an irrigation boom or other irrigation system 410 through another fluid connector 407. In an implementation, the lab 400 may be fluidly connected to the irrigation system 410 through a fluid connector 406 for convenience such that nanoparticulated fertilizer containing fluid can be dispersed in an irrigation system 410.

It will be appreciated that in any implementation the lab 400 may be a clean room having all the properties of any clean lab, such that undesirable particles or compounds are not introduced into the nanoparticulated or manipulated fertilizer as discussed more fully herein.

As can be seen in the figure and realized by the discussion that followed, the amount of fertilizer that is effective can be greatly reduced by preparing nanoparticulated fertilizer proximate to the crop that is to be fertilized with the use of a mobile lab.

Figure 2:
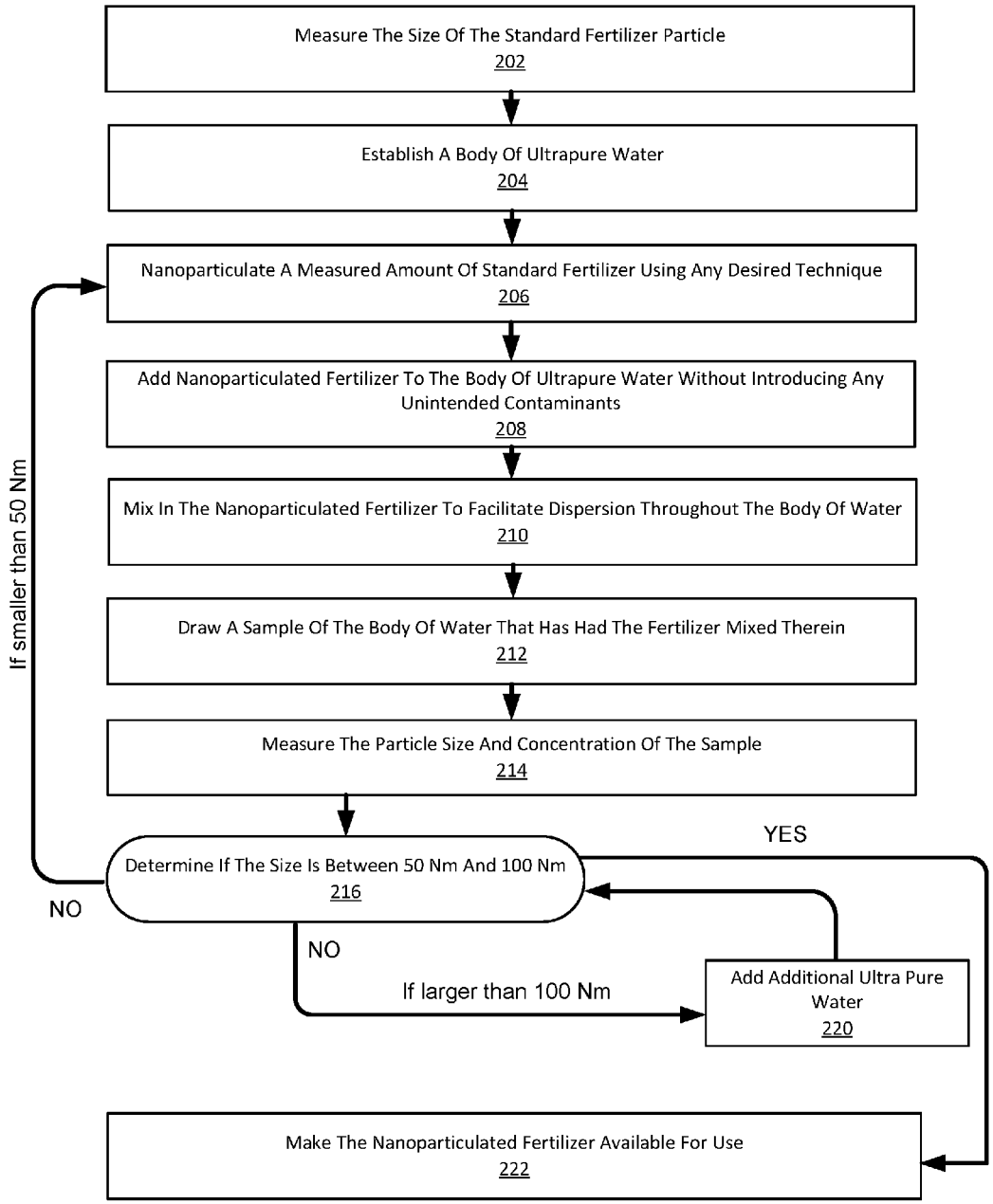
FIG. 2 is a flow chart of an implementation of methods and operations in accordance with the principles of the disclosure.
Figure 3A:
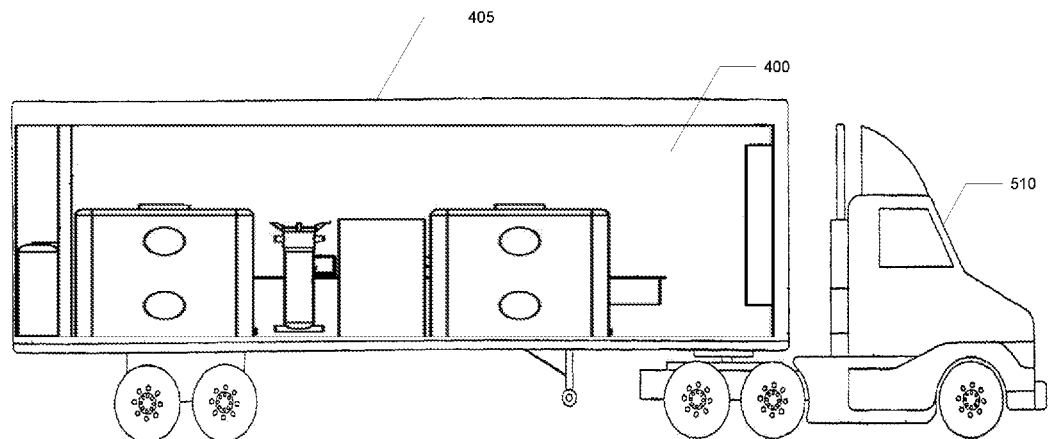
FIG. 3A illustrates a schematic view of a mobile fertilizing system configured for transporting to a site.
Figure 3B:
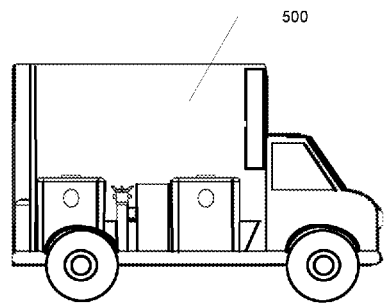
FIG. 3B illustrates a schematic view of a mobile fertilizing system configured for transporting to a site.
Figure 3C:
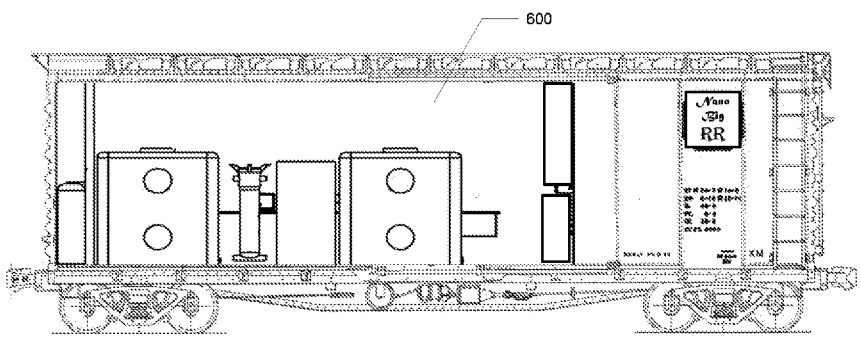
FIG. 3C illustrates a schematic view of a mobile fertilizing system configured for transporting to a site.
Figure 4:
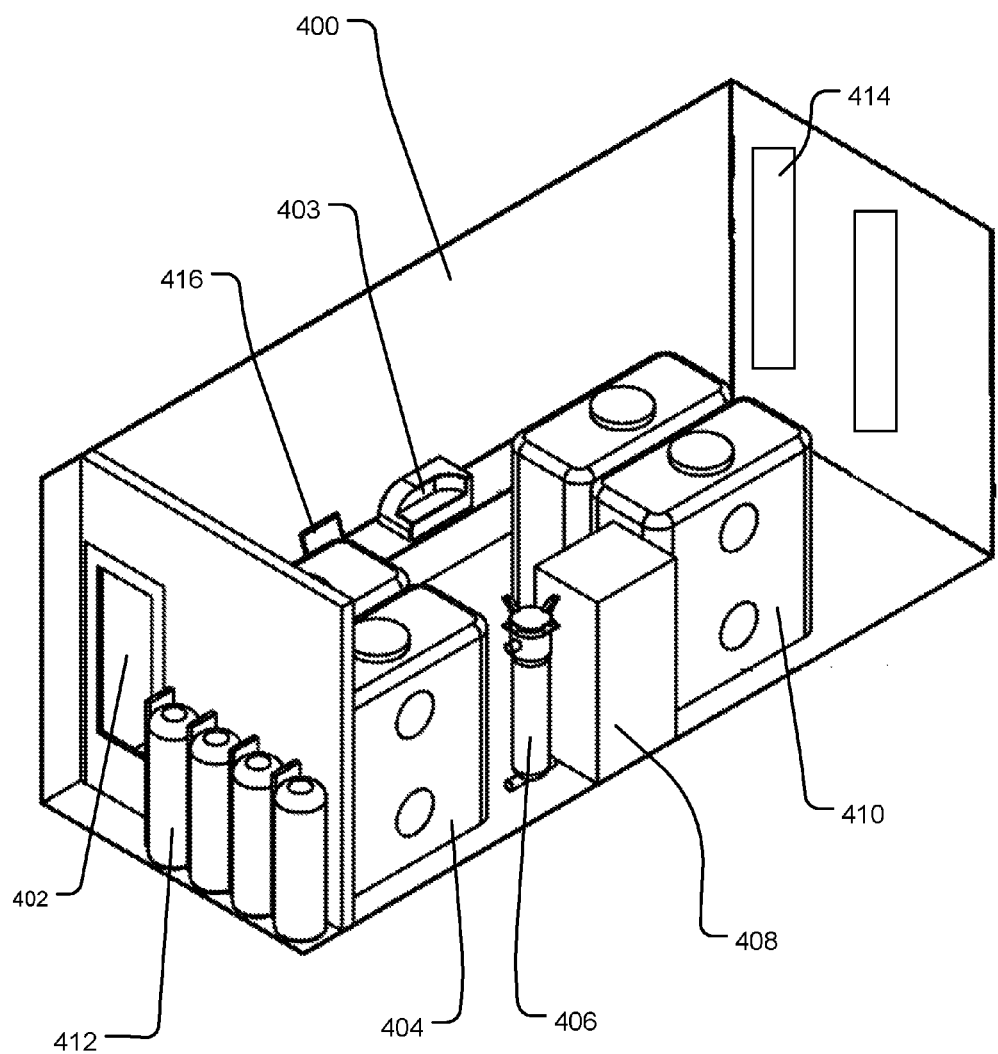
FIG. 4 illustrates an open view of a fertilizer particulation lab showing an implementation of the principle of the disclosure.

Referring now to FIG. 2, a method for providing nanoparticulated fertilizer at or near the location where the nanoparticulated fertilizer is used will be discussed. FIG. 2 illustrates a flow chart of processes that a mobile lab may employ to produce a highly effective nanoparticulated fertilizer that may be held, stored and/or delivered in a fluid form. A fertilizer composition may be measured to determine the standard particle size of the fertilizer in its standard form. Many fertilizers may come in pellets, grain structures, sand like structures, etc. and may also be found in a liquid form. Liquid fertilizers may be advantageous because it has the ability to spread the fertilizer more effectively and evenly than a granular fertilizer can be spread. Regardless of the standard particle size of current fertilizers, in the implementation the absorption rate by plants can be improved by making the particle smaller. For example, the disclosure contemplates reducing the chemical moiety or compound size to 100 nanometers or less, or even 50 nanometers or less, in order to increase uptake into the cell. In an implementation, a nano-sized fertilizer particle implemented into a compound that is 100 nanometers or less is desired for the most effective absorption.

At 204, the system 200 may nanoparticulate the fertilizer composition. Any known method for nano-sizing particles is considered to be within the scope of this disclosure. Additionally, because of the advantages of the methods and systems as disclosed herein, much less fertilizer needs to be handled such that a mobile lab configuration is more than capable of processing the particles into nano-sized particles. It is to be considered within the scope of the disclosure to contemplate fertilizer in any physical state such as for example, solid, liquid, and gas. In an implementation, regardless of the physical state of the fertilizer, in its nanoparticulated form it may be mixed into and suspended within water without the fertilizer composition breaking down or dissolving into the water.

The system and method of nanoparticulating specific fertilizer nutrients may comprise, but is not necessarily limited to, nanoparticulating "N" (Nitrogen), "P" (Phosphorus) and "K" (Potassium, a.k.a potassium chloride or muriate of potash), wherein these nutrients may be suspended or dissolved or in some other fashion included in a high-purity water base.

The agricultural industry relies heavily upon NPK fertilizers in varying relative amounts to produce a desired result for crop development and growth. Different plant types, different soil types, different climate and temperate zones necessitate the need for various concentrations of these three elements or nutrients, namely NPK. It will be appreciated that other nutrients may be added to the NPK concentrations, either on a macro, micro or nano nutrient scale and are intended to fall within the scope of the disclosure.

It should be noted that the use of the terms NPK in the disclosure (which represent nitrogen, phosphorous, and potassium) are used in the manner that the fertilizer industry that services the agricultural industry uses those terms. Thus, it will be appreciated that before modern lab instrumentation was developed, chemists used a gravimetric (weighing) method after ignition to determine the phosphorus and potassium content of fertilizers in the form of phosphorus oxide (P2O5) and potassium oxide (K2O). By convention, the amounts (or analysis grade) of phosphorus and potassium in fertilizers are still expressed in this oxide form. The Association of American Plant Food Control officials have developed a uniform state fertilizer bill which says that available P2O5 and soluble K2O must be guaranteed by the manufacturer and so the guaranteed analysis must still be expressed in the oxide form. Nitrogen content has always been expressed as simply N.

According to the conventional fertilizer standards and by way of illustration, a 100 pound bag of 10-10-10 contains 10% or 10 pounds of nitrogen, 10% or 10 pounds of P2O5 and 10% or 10 pounds of K2O. Since P2O5 is really only 44% actual elemental phosphorus and K2O is only 83% actual elemental potassium, a 100 pound bag of 10-10-10 contains 10% or 10 pounds of nitrogen, 4.4% or 4.4 pounds of elemental phosphorus and 8.3% or 8.3 pounds of elemental potassium.

Perhaps the reluctance of the fertilizer industry to convert to expressing the nutrients in the elemental forms is due to the perception that less fertilizer is being purchased for the same amount of money. A 100 pound bag of 10-10-10 containing N, P2O5 and K2O would be equivalent to a 100 pound bag of 10-4.4-8.3 containing N, P and K.

Once the fertilizer is added to the soil, the oxide forms, P2O5 and K2O, are no longer used when discussing these two nutrients. The amount of these nutrients analyzed in the soil may be expressed as the pounds per acre of P and K.

Typical NPK containing composition may comprise the following, but are not limited to:

82-00-00 Anhydrous Ammonia
21-0-0 Ammonium Sulfate
46-0-0 Urea
35-0-0 Ureaform (~85% slow release, sparingly soluble ureaformaldehyde)
40-0-0 Methylene Ureas (~70% slow release)
31-0-0 IsobutylideneDiurea (~90% slow release)
30-0-0 to 40-00-00 Sulfur-coated Urea (slow release)
33-0-0 Ammonium Nitrate
15-0-0 Calcium Nitrate
13-0-44 Potassium Nitrate
0-17-0 to 0-22-0 Superphosphate (Monocalcium phosphate monohydrate with gypsum)
0-44-0 to 0-52-0 Triple superphosphate (Monocalcium phosphate monohydrate)
10-34-0 to 11-37-0 Ammonium Polyphosphate
11-48-0 to 11-55-0 Monoammonium Phosphate
18-46-0 to 21-54-0 Diammonium Phosphate
28-0-0
32-0-0
12-0-0
10-0-0
7-21-7
4-10-10
8-21-4
9-18-4
9-20-2
18-13-0
10-30-0

It will be understood that the composition of the disclosure includes any and all NPK containing fertilizer combinations that are currently known and that may become known in the future without departing from the scope of the disclosure, including those found on the Kansas Department of Agriculture listing fertilizer products per fertilizer manufacture. Thus, the disclosure requires only a fraction of the manipulated fertilizer compared with the standard fertilizer used in the industry.

At 204, the system 200 may establish a body of pure water for receiving the nanoparticulated fertilizer compound therein. It will be appreciated that the method contemplates manufacturing or producing ultrapure water at 204.

At 206, as the water is increasingly purified it may become more reactive with particulates available in the environment. Accordingly, the established body of ultrapure water may be housed in an air tight container (as seen in FIG. 4) that prevents atmospheric contaminants from stabilizing the water molecules within the body of ultrapure water. The unstable state of the water is desirable because it will readily receive a nano-sized fertilizer particle therein such that the fertilizer particle is suspended by, and stabilizes, a plurality of water molecules.

At 208, the system adds the nanoparticulated fertilizer composition into the body of ultrapure water to create a mixture of fertilizer and water referred to herein as a fertilizer mixture. It should be noted that in an implementation, the adding process may be sealed against the surrounding atmosphere such that the reactive ultrapure water can stabilize around a nanoparticle of fertilizer rather than a contamination particle. In other words, by isolating the mixing process against the atmosphere and any contaminate particles contained within the atmosphere, the nano-sized fertilizer particle from 204 has a very high probability of becoming the nucleus of a plurality of water molecules. In this regard, protecting against inadvertent introduction of contaminants of particles into the ultrapure water while introducing the particulated fertilize is an important aspect that should be considered. Accordingly, a clean room environment should be used.

At 210, the system 200 may mix the fertilizer mixture in order to provide an even dispersion of the fertilizer nanoparticles within the body of ultrapure water. The mixing process may be any process that adds energy into the mixture thereby prolonging the agglomeration, or re-agglomeration of the water molecules about a fertilizer nanoparticle, thereby allowing a modicum of control over the stabilized molecular structures within the body of ultrapure water. It will be appreciated that the nanoparticles or nano-sized fertilizer particles are free of any chemical side chain and free of any micelle used to protect the nanoparticles or nano-sized particles from re-agglomeration.

At 212, the system 200 may sample the fertilizer mixture to determine the amount of dispersion of the fertilizer nanoparticles throughout the body of ultrapure water. At 214, the system may further use the sample drawn at 212 to determine the size of the fertilizer nanoparticles within the mixture. Additionally, at 216 the system may determine the concentration of the fertilizer particles within the fertilizer mixture. In an implementation, such determinations may be made by a trained human person and/or a computer, or any combination of the two.

At 216, if the system (or operator of the system) determines that the fertilizer nanoparticles or resulting molecular structures fall outside a desired range of about 50 nanometers to about 100 nanometers within the mixture and discovers the fertilizer particles or resulting molecular structures are too large (larger than about 100 nanometers in any one dimension) for the application at hand, the fertilizer mixture can be further processed, by further reducing the fertilizer nanoparticle size at 206 or by adding additional ultrapure water into the mixture at 220 to reduce the size of the resulting structures within the fertilizer mixture.

At 216, if it is determined that the size of the fertilizer nanoparticles or resulting molecular structures are within the range of about 50 nanometers and about 100 nanometers, and it is determined that is the appropriate or desired size and concentration of fertilizer, which has now been achieved, then the fertilizer mixture is ready for use at 222.

At, 216 if it is determined that the size of the fertilizer nanoparticles or resulting molecular structures are smaller than about 50 nanometers, then additional nanoparticulated particles may be added into the fertilizer mixture to increase the size and concentration of nanoparticulated fertilizer into the fertilizer mixture at 206. For example, at 216 the size of the fertilizer nanoparticulate and/or the chemical moiety of the fertilizer compound may be measured. The disclosure contemplates reducing the size of the fertilizer nanoparticulate and/or the chemical moiety of the fertilizer compound to 100 nanometers or less, or even 50 nanometers or less, to achieve a desired size and concentration. A range of about 50 nanometers and 100 nanometers has been shown and determined to be a suitable size and concentration range for agricultural applications. However, larger or smaller size and concentration ranges are contemplated by the disclosure.

On the other hand, if at 216 the system determines that the fertilizer nanoparticles or resulting molecular structures within the mixture are acceptable for the application at hand, the optimized fertilizer mixture can be applied to the crop at 222. In an implementation, the mobile lab may be in fluid communication with an irrigation system, or other fluid dispersion system, whether through a storage container or otherwise in direct communication, such that a fertilizer mixture can be directly introduced within the irrigation system.

FIGS. 3A-3C illustrate mobile labs 400, 500, 600, respectively, which can be transported by or within a motorized vehicle 510, such as a truck or tractor, or by railroad or other trailer configurations. In an implementation, the motorized vehicle 510 may leave the mobile lab proximate to the crops that are to be treated for a predetermined treatment period. Furthermore, an implementation may include the rotation and relocation of labs that are configured to specifically correspond to various maturation stages of a crop, or a plurality of crops.

Additionally, various security measures may be included for a mobile lab. The security measures may range from security personnel to product and equipment self-destruct protocols to protect the formulation of fertilizer mixtures and to secure the potent and possibly dangerous nanoparticle fertilizer. FIG. 4 illustrates an embodiment of a clean environment for the lab that may be mobilized by its placement within a trailer or train car or the like. As seen in FIG. 4, the lab 400 may include an access and security door 402 for ingress and egress from the lab 400. The lab 400 may comprise equipment for manipulating standard fertilizer as discussed herein, including a nano sizer 403, one or a plurality of source fluid (which may be water) holding tanks or containers 404, a filter 406, a reverse osmosis filter 408, one or more holding tanks or containers 410 for receiving manipulated fluids therein, a deionized system and tanks 412, a mixing device or system 414 for mixing nanoparticulates into ultrapure water, and a computer and instrumentation 416 for measuring the relative sizes of the nanoparticles and manipulated fertilizer mixture.

In the foregoing Detailed Description of the Disclosure, various features of the disclosure are grouped together in a single embodiment for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description of the Disclosure by this reference, with each claim standing on its own as a separate embodiment of the disclosure.

It is to be understood that the above-described arrangements are only illustrative of the application of the principles of the disclosure. Numerous modifications and alternative arrangements may be devised by those skilled in the art without departing from the spirit and scope of the disclosure and the appended claims are intended to cover such modifications and arrangements. Thus, while the disclosure has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A nanoparticulated fertilizer composition comprising:

an effective amount of a nanoparticulated nitrogen-rich material as per a first volume of aqueous solution;

an effective amount of a nanoparticulated phosphorus-rich material as per a first volume of aqueous solution;

an effective amount of a nanoparticulated potassium-rich material as per a first volume of aqueous solution;

wherein the nitrogen-rich material, the phosphorus-rich material and potassium-rich material are added to an amount of ultrapure water to thereby create the first volume of aqueous solution; and wherein an effective amount of the nanoparticulated fertilizer composition is less than 50% of a corresponding standard fertilizer composition for a predetermined application rate.

2. The fertilizer composition of claim 1, wherein the effective amount of the nitrogen-rich material contained within the nanoparticulated fertilizer composition is less than 50% nitrogen of a corresponding standard fertilizer composition.

3. The fertilizer composition of claim 1, wherein the effective amount of the phosphorus-rich material contained within the nanoparticulated fertilizer composition is less than 50% phosphorus of a corresponding standard fertilizer composition.

4. The fertilizer composition of claim 1, wherein the effective amount of the potassium-rich material contained within the nanoparticulated fertilizer composition is less than 50% potassium of a corresponding standard fertilizer composition.

5. The fertilizer composition of claim 1, wherein the effective amount of the nanoparticulated fertilizer composition is less than 5% of a corresponding standard fertilizer composition.

6. The fertilizer composition of claim 5, wherein the effective amount of the nitrogen-rich material within the nanoparticulated fertilizer composition is less than 5% of nitrogen in a corresponding standard fertilizer composition.

7. The fertilizer composition of claim 5, wherein the effective amount of the phosphorus-rich material within the nanoparticulated fertilizer composition is less than 5% of phosphorus in a corresponding standard fertilizer composition.

8. The fertilizer composition of claim 5, wherein the effective amount of the potassium-rich material within the nanoparticulated fertilizer composition is less than 5% of potassium in a corresponding standard fertilizer composition.

9. The fertilizer composition of claim 1, wherein the ultrapure water comprises a purity level that falls within a range of about 12 mega ohms to about 18.3 mega ohms.

\* \* \* \* \*